US008122542B2

(12) United States Patent
Reitz et al.

(10) Patent No.: US 8,122,542 B2
(45) Date of Patent: Feb. 28, 2012

(54) PATIENT SUPPORT DEVICE

(75) Inventors: Graham T. Reitz, Madison, WI (US);
Bradley J. Brunker, Madison, WI (US);
Ralph J. Gable, Oregon, WI (US);
Wayne L. Staats, Jr., Cambridge, MA (US); Brent Harper, Mazomanie, WI (US)

(73) Assignee: Tomotherapy Incorporated, Madison, WI (US)

( * ) Notice: Subject to any disclaimer, the term of this patent is extended or adjusted under 35 U.S.C. 154(b) by 0 days.

(21) Appl. No.: 12/204,641

(22) Filed: Sep. 4, 2008

(65) Prior Publication Data
US 2009/0056022 A1   Mar. 5, 2009

Related U.S. Application Data

(60) Provisional application No. 60/969,904, filed on Sep. 4, 2007.

(51) Int. Cl.
*A47B 13/00* (2006.01)

(52) U.S. Cl. .................. 5/601; 5/600; 378/209

(58) Field of Classification Search .............. 5/600, 601; 378/20, 209
See application file for complete search history.

(56) References Cited

U.S. PATENT DOCUMENTS

| | | | |
|---|---|---|---|
| 3,497,786 A | | 2/1970 | Lombardo |
| 4,131,802 A | * | 12/1978 | Braden et al. .................. 378/20 |
| 5,008,907 A | | 4/1991 | Norman et al. |
| 5,044,354 A | | 9/1991 | Goldhorn et al. |
| 5,113,420 A | | 5/1992 | Davis, Jr. et al. |
| 5,210,893 A | * | 5/1993 | Uosaki et al. ..................... 5/601 |
| 5,317,616 A | | 5/1994 | Swerdloff et al. |
| 5,351,280 A | | 9/1994 | Swerdloff et al. |
| 5,442,675 A | | 8/1995 | Swerdloff et al. |
| 5,446,548 A | | 8/1995 | Gerig et al. |
| 5,528,650 A | | 6/1996 | Swerdloff et al. |
| 5,548,627 A | | 8/1996 | Swerdloff et al. |
| 5,625,663 A | | 4/1997 | Swerdloff et al. |
| 5,647,663 A | | 7/1997 | Holmes |
| 5,651,043 A | | 7/1997 | Tsuyuki et al. |
| 5,657,498 A | * | 8/1997 | Hum ................................ 5/601 |
| 5,661,773 A | | 8/1997 | Swerdloff et al. |
| 5,751,781 A | | 5/1998 | Brown et al. |
| 5,754,622 A | | 5/1998 | Hughes |
| 5,754,623 A | | 5/1998 | Seki |

(Continued)

FOREIGN PATENT DOCUMENTS

CA    2091275    9/1993

(Continued)

OTHER PUBLICATIONS

Extended Search Report from European Patent Office for Application No. 08799173.3 dated Apr. 15, 2011.

(Continued)

*Primary Examiner* — Robert G Santos
*Assistant Examiner* — Brittany Wilson
(74) *Attorney, Agent, or Firm* — Michael Best & Friedrich LLP

(57) ABSTRACT

A method and system configured to substantially synchronize two opposite ends of a table assembly of a radiation therapy treatment system. The system includes a lateral motion control system coupled to the table assembly and configured to detect positions of the two opposite ends of the table assembly and to substantially synchronize the positions as the table assembly is laterally moved with respect to a gantry of the radiation therapy treatment system.

20 Claims, 13 Drawing Sheets

U.S. PATENT DOCUMENTS

| | | | |
|---|---|---|---|
| 5,835,562 A | 11/1998 | Ramsdell et al. | |
| 6,045,262 A | 4/2000 | Igeta et al. | |
| 6,152,599 A | 11/2000 | Salter, Jr. | |
| 6,155,976 A * | 12/2000 | Sackner et al. | 600/300 |
| 6,217,214 B1 | 4/2001 | Cabral et al. | |
| 6,442,777 B1 | 9/2002 | Pauli | |
| 6,615,428 B1 | 9/2003 | Pattee | |
| 6,634,790 B1 | 10/2003 | Salter, Jr. | |
| 6,637,056 B1 | 10/2003 | Tybinkowski et al. | |
| 6,769,145 B1 | 8/2004 | Pfeuffer et al. | |
| 6,929,398 B1 | 8/2005 | Tybinkowski et al. | |
| 6,955,464 B1 | 10/2005 | Tybinkowski et al. | |
| 7,008,105 B2 | 3/2006 | Amann et al. | |
| 7,077,569 B1 | 7/2006 | Tybinkowski et al. | |
| 7,116,749 B2 | 10/2006 | Besson | |
| 7,120,223 B2 * | 10/2006 | Nafstadius | 5/601 |
| 7,302,038 B2 | 11/2007 | Mackie et al. | |
| 7,552,490 B2 | 6/2009 | Saracen et al. | |
| 2003/0222617 A1 * | 12/2003 | Nakai et al. | 318/701 |
| 2004/0057557 A1 | 3/2004 | Nafstadius | |
| 2004/0172756 A1 * | 9/2004 | Somasundaram | 5/600 |
| 2005/0129181 A1 | 6/2005 | Shinoda | |
| 2006/0042009 A1 | 3/2006 | Somasundaram et al. | |
| 2008/0235873 A1 * | 10/2008 | Farooqui | 5/601 |
| 2008/0279328 A1 | 11/2008 | Zeitler et al. | |
| 2009/0070935 A1 | 3/2009 | Brunker et al. | |
| 2010/0319128 A1 | 12/2010 | Kuro et al. | |

FOREIGN PATENT DOCUMENTS

| | | |
|---|---|---|
| JP | 11313900 | 11/1999 |
| WO | 2005041835 | 5/2005 |
| WO | 2007127970 | 11/2007 |

OTHER PUBLICATIONS

PCT/US2008/075269 International Search Report and Written Opinion dated Feb. 11, 2009.

* cited by examiner

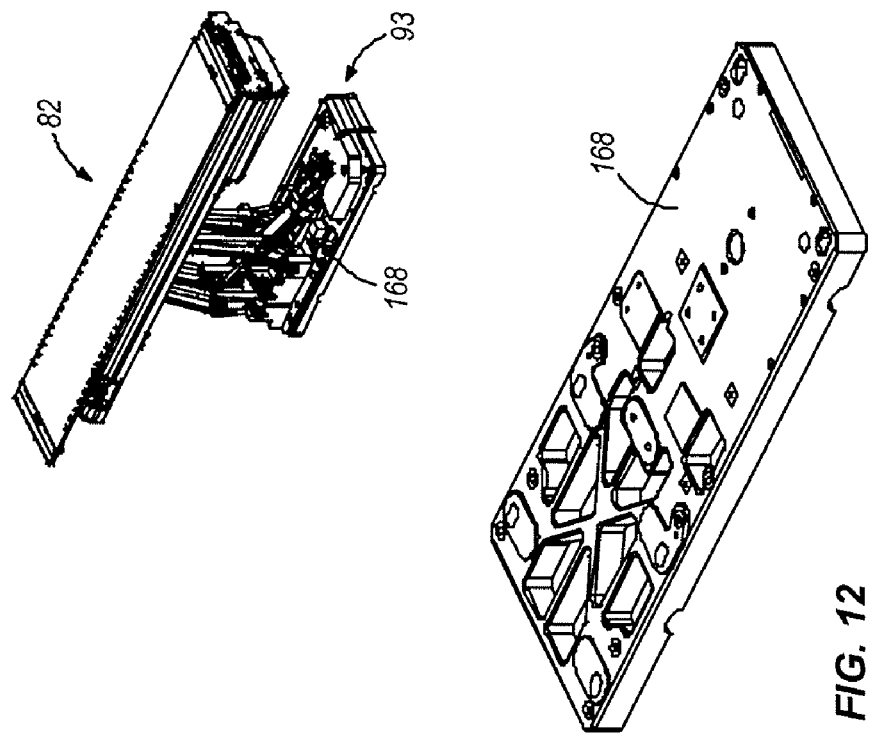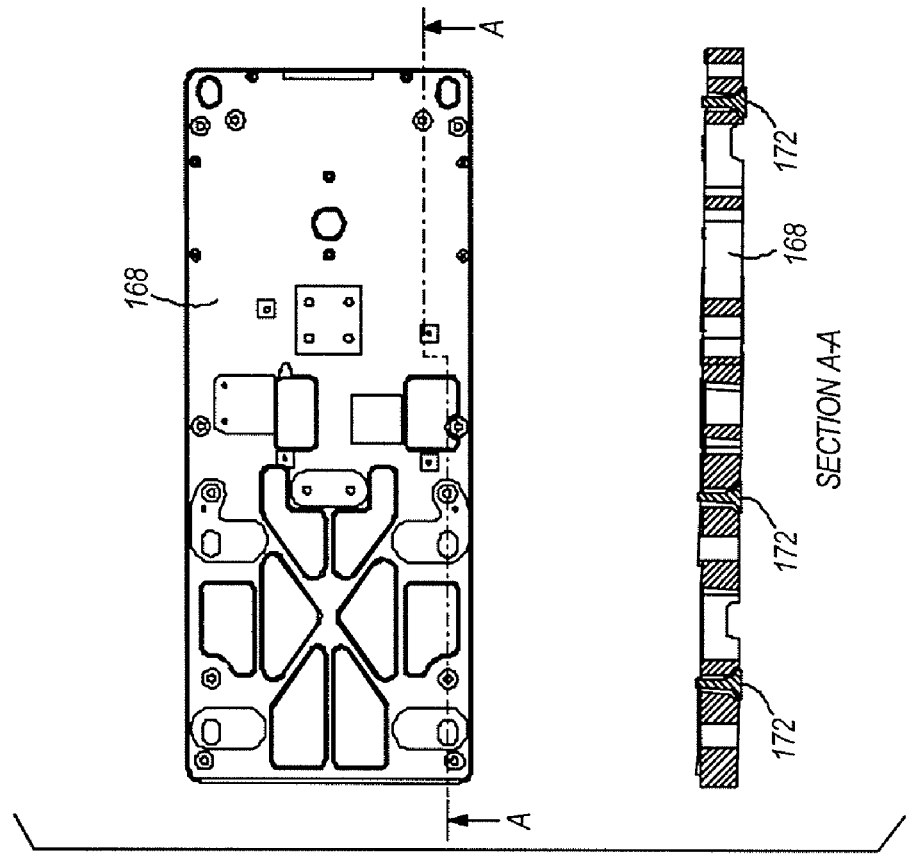
FIG. 12

PATIENT SUPPORT DEVICE

RELATED APPLICATIONS

This application claims priority to U.S. Provisional Patent Application Ser. No. 60/969,904, filed Sep. 4, 2007, the entire contents of which are incorporated herein by reference.

FIELD OF THE INVENTION

The invention relates to a radiation therapy imaging and treatment system. More specifically, the invention relates to a patient support device for use with such a system having improved motion control.

BACKGROUND

Medical equipment for radiation therapy treats tumorous tissue with high energy radiation. The dose and the placement of the dose must be accurately controlled to ensure both that the tumor receives sufficient radiation to be destroyed, and that damage to the surrounding and adjacent non-tumorous tissue is minimized. Intensity modulated radiation therapy (IMRT) treats a patient with multiple rays of radiation each of which may be independently controlled in intensity and/or energy. The rays are directed from different angles about the patient and combine to provide a desired dose pattern. In external source radiation therapy, a radiation source external to the patient treats internal tumors. The external source is normally collimated to direct a beam only to the tumorous site. Typically, the radiation source consists of either high-energy X-rays, electrons from certain linear accelerators, or gamma rays from highly focused radioisotopes, though other types of radiation sources are possible.

One way to control the position of the radiation delivery to the patient is through the use of a patient support device, such as a couch, that is adjustable in one or more directions. The use of a patient support device is well known in the medical field, with similar patient support devices being used in CT scanning devices and Magnetic Resonances Imagers (MRIs). The patient support device allows the patient to be moved into and out of the field of the radiation to be delivered and in some cases, allow for adjustments of patient position during a radiation treatment.

SUMMARY

When a patient support device such as a couch is used in this manner, there are many variables that need to be accounted for. For example construction materials and configuration of suitable electronics necessary to operate the couch must be carefully selected to ensure smooth operation of the couch, and precise measurement of couch position (when the couch has multiple movable parts). When these features are thoughtfully considered in the environment of radiation delivery, the patient support device can be a key tool in improving patient outcomes.

In one embodiment, the present invention provides a patient support device including a base, a table assembly, a controller, and a lateral motion control system. The table assembly is configured to support a patient and includes a lower support, and an upper support movable with respect to the lower support, the upper support including a first end and a second end. The controller is electrically coupled to the table assembly and is configured to instruct the table assembly to move in a first direction along an axis, in a lateral direction with respect to the axis, and in a vertical direction with respect to the axis. The lateral motion control system is electrically coupled to the table assembly and includes a first motor including a shaft coupled to the first end of the upper support, a first encoder coupled to the shaft and configured to detect a first position of the shaft of the first motor, a second motor including a shaft coupled to the second end of the upper support, and a second encoder coupled to the shaft and configured to detect a second position of the shaft of the second motor, the controller configured to receive and compare the first position and the second position, the controller configured to communicate instructions to the first motor and the second motor to substantially synchronize the first position and the second position.

In another embodiment, the invention provides a radiation therapy treatment system comprising a gantry, a table assembly configured to support a patient, a controller, and a lateral motion control system. The table assembly includes a lower support, and an upper support movable with respect to the lower support, the upper support including a first end and a second end. The controller is electrically coupled to the table assembly and is configured to instruct the table assembly to move in a first direction into the gantry, in a lateral direction with respect to the first direction, and in a vertical direction with respect to the first direction. The lateral motion control system is electrically coupled to the table assembly and is configured to detect a position of the first end of the upper support and a position of the second end of the upper support and output the positions of the first end and the second end.

In another aspect of the invention, the present invention provides a method including the acts of detecting a position of a first end of a table assembly for a radiation therapy treatment system, detecting a position of a second end of the table assembly, comparing the position of the first end with the position of the second end, and substantially synchronizing the position of the first end with the position of the second end.

Other aspects of the invention will become apparent by consideration of the detailed description and accompanying drawings.

BRIEF DESCRIPTION OF THE DRAWINGS

FIG. 12 illustrates a riser of the patient support device of FIG. 3.

DETAILED DESCRIPTION

Figure 1:
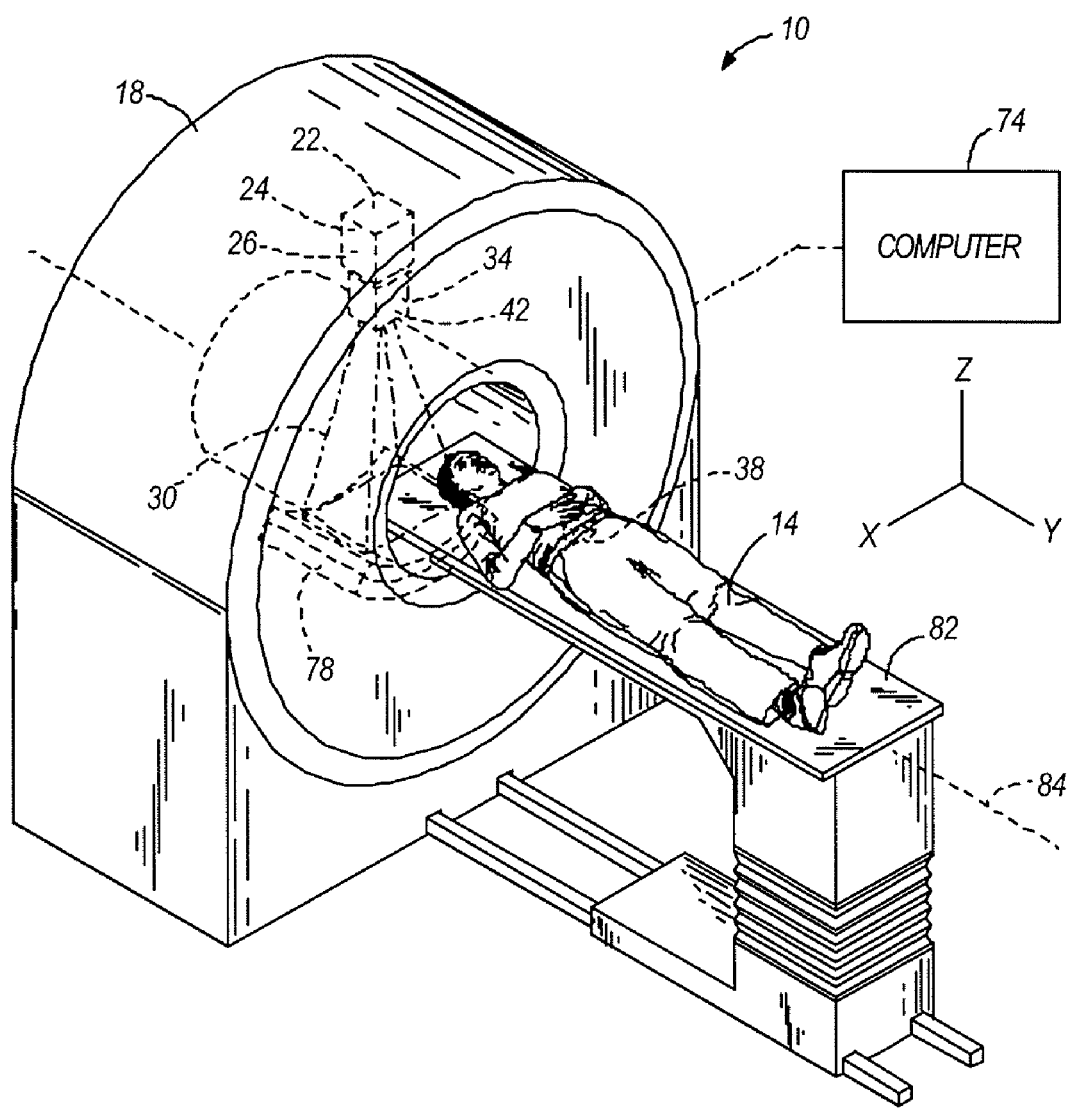
FIG. 1 is a perspective view of a radiation therapy treatment system.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first," "second," and "third" are used herein for purposes of description and are not intended to indicate or imply relative importance or significance.

In addition, it should be understood that embodiments of the invention include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

FIG. 1 illustrates a radiation therapy treatment system 10 that can provide radiation therapy to a patient 14. The radiation therapy treatment can include photon-based radiation therapy, brachytherapy, electron beam therapy, proton, neutron, or particle therapy, or other types of treatment therapy. The radiation therapy treatment system 10 includes a gantry 18. The gantry 18 can support a radiation module 22, which can include a radiation source 24 and a linear accelerator 26 (a.k.a. "a linac") operable to generate a beam 30 of radiation. Though the gantry 18 shown in the drawings is a ring gantry, i.e., it extends through a full 360° arc to create a complete ring or circle, other types of mounting arrangements may also be employed. For example, a C-type, partial ring gantry, or robotic arm could be used. Any other framework capable of positioning the radiation module 22 at various rotational and/or axial positions relative to the patient 14 may also be employed. In addition, the radiation source 24 may travel in path that does not follow the shape of the gantry 18. For example, the radiation source 24 may travel in a non-circular path even though the illustrated gantry 18 is generally circular-shaped. The gantry 18 of the illustrated embodiment defines a gantry aperture 32 into which the patient 14 moves during treatment.

The radiation module 22 can also include a modulation device 34 operable to modify or modulate the radiation beam 30. The modulation device 34 provides the modulation of the radiation beam 30 and directs the radiation beam 30 toward the patient 14. Specifically, the radiation beam 30 is directed toward a portion 38 of the patient. Broadly speaking, the portion may include the entire body, but is generally smaller than the entire body and can be defined by a two-dimensional area and/or a three-dimensional volume. A portion or area desired to receive the radiation, which may be referred to as a target or target region, is an example of a region of interest. Another type of region of interest is a region at risk. If a portion includes a region at risk, the radiation beam is preferably diverted from the region at risk. Such modulation is sometimes referred to as intensity modulated radiation therapy ("IMRT").

Figure 2:
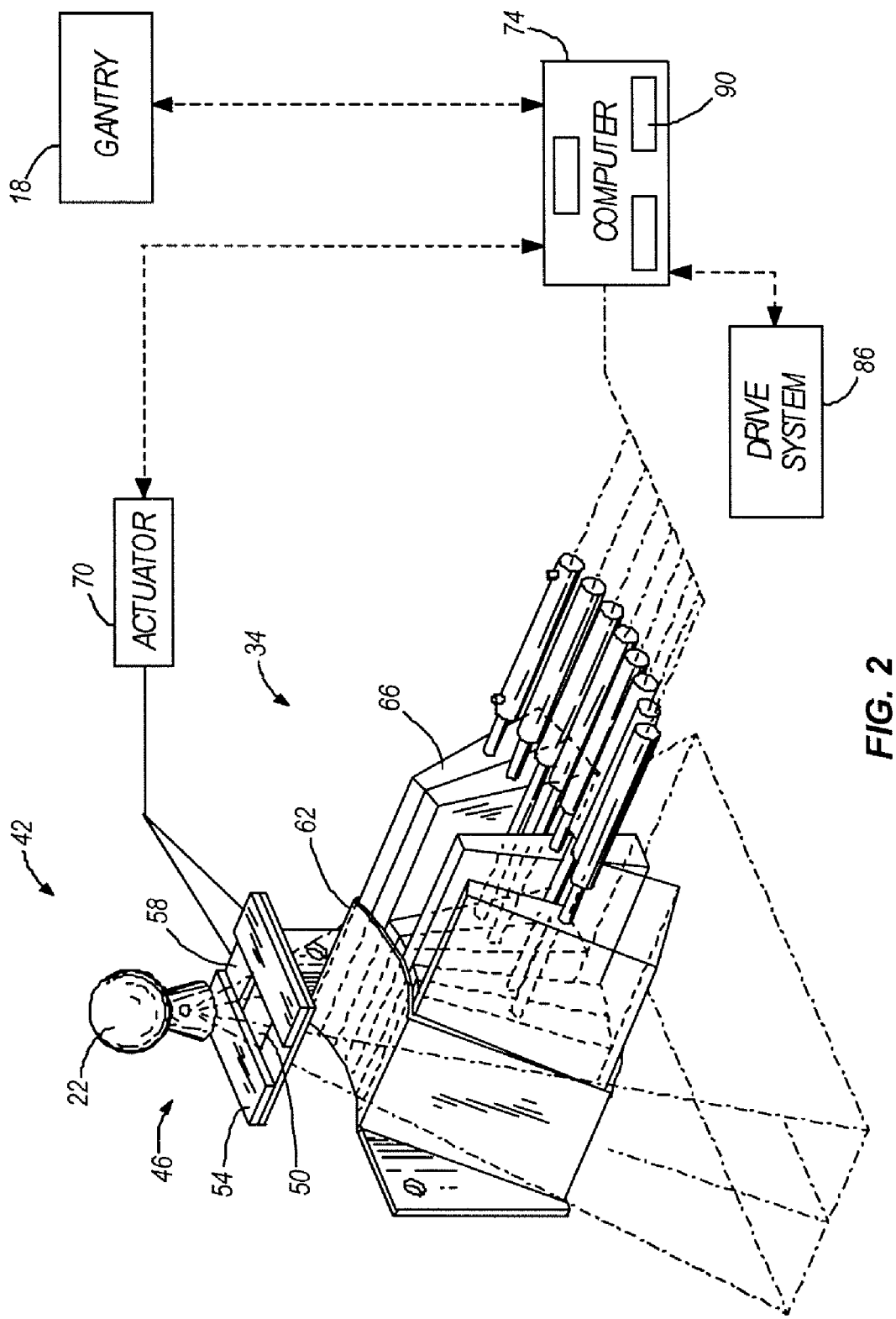
FIG. 2 is a perspective view of a multi-leaf collimator that can be used in the radiation therapy treatment system illustrated in FIG. 1.
Figure 3:
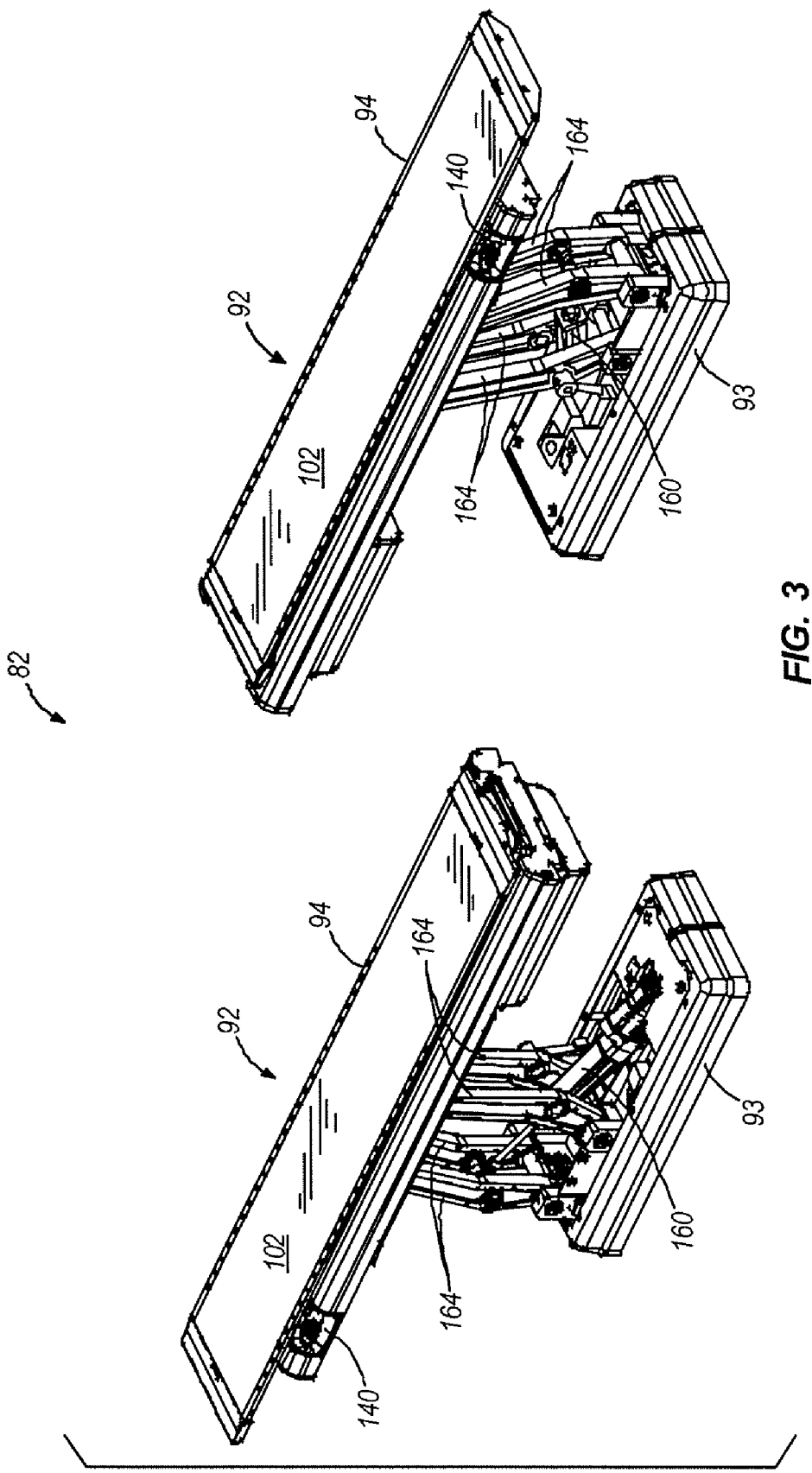
FIG. 3 is a perspective view of a patient support device for use with the system of FIG. 1.

The modulation device 34 can include a collimation device 42 as illustrated in FIG. 2. The collimation device 42 includes a set of jaws 46 that define and adjust the size of an aperture 50 through which the radiation beam 30 may pass. The jaws 46 include an upper jaw 54 and a lower jaw 58. The upper jaw 54 and the lower jaw 58 are moveable to adjust the size of the aperture 50. The position of the jaws 46 regulates the shape of the beam 30 that is delivered to the patient 14.

In one embodiment, and illustrated in FIG. 2, the modulation device 34 can comprise a multi-leaf collimator 62 (a.k.a. "MLC"), which includes a plurality of interlaced leaves 66 operable to move from position to position, to provide intensity modulation. It is also noted that the leaves 66 can be moved to a position anywhere between a minimally and maximally-open position. The plurality of interlaced leaves 66 modulate the strength, size, and shape of the radiation beam 30 before the radiation beam 30 reaches the portion 38 on the patient 14. Each of the leaves 66 is independently controlled by an actuator 70, such as a motor or an air valve so that the leaf 66 can open and close quickly to permit or block the passage of radiation. The actuators 70 can be controlled by a computer 74 and/or controller.

The radiation therapy treatment system 10 can also include a detector 78, e.g., a kilovoltage or a megavoltage detector, operable to receive the radiation beam 30, as illustrated in FIG. 1. The linear accelerator 26 and the detector 78 can also operate as a computed tomography (CT) system to generate CT images of the patient 14. The linear accelerator 26 emits the radiation beam 30 toward the portion 38 in the patient 14. The portion 38 absorbs some of the radiation. The detector 78 detects or measures the amount of radiation absorbed by the portion 38. The detector 78 collects the absorption data from different angles as the linear accelerator 26 rotates around and emits radiation toward the patient 14. The collected absorption data is transmitted to the computer 74 to process the absorption data and to generate images of the patient's body tissues and organs. The images can also illustrate bone, soft tissues, and blood vessels. The system 10 can also include a patient support device, shown as a couch 82, operable to support at least a portion of the patient 14 during treatment. While the illustrated couch 82 is designed to support the entire body of the patient 14, in other embodiments of the invention the patient support need not support the entire body, but rather can be designed to support only a portion of the patient 14 during treatment. The couch 82 moves into and out of the field of radiation along an axis 84 (i.e., Y axis). The couch 82 is also capable of moving along the X and Z axes as illustrated in FIG. 1.

Figure 4:
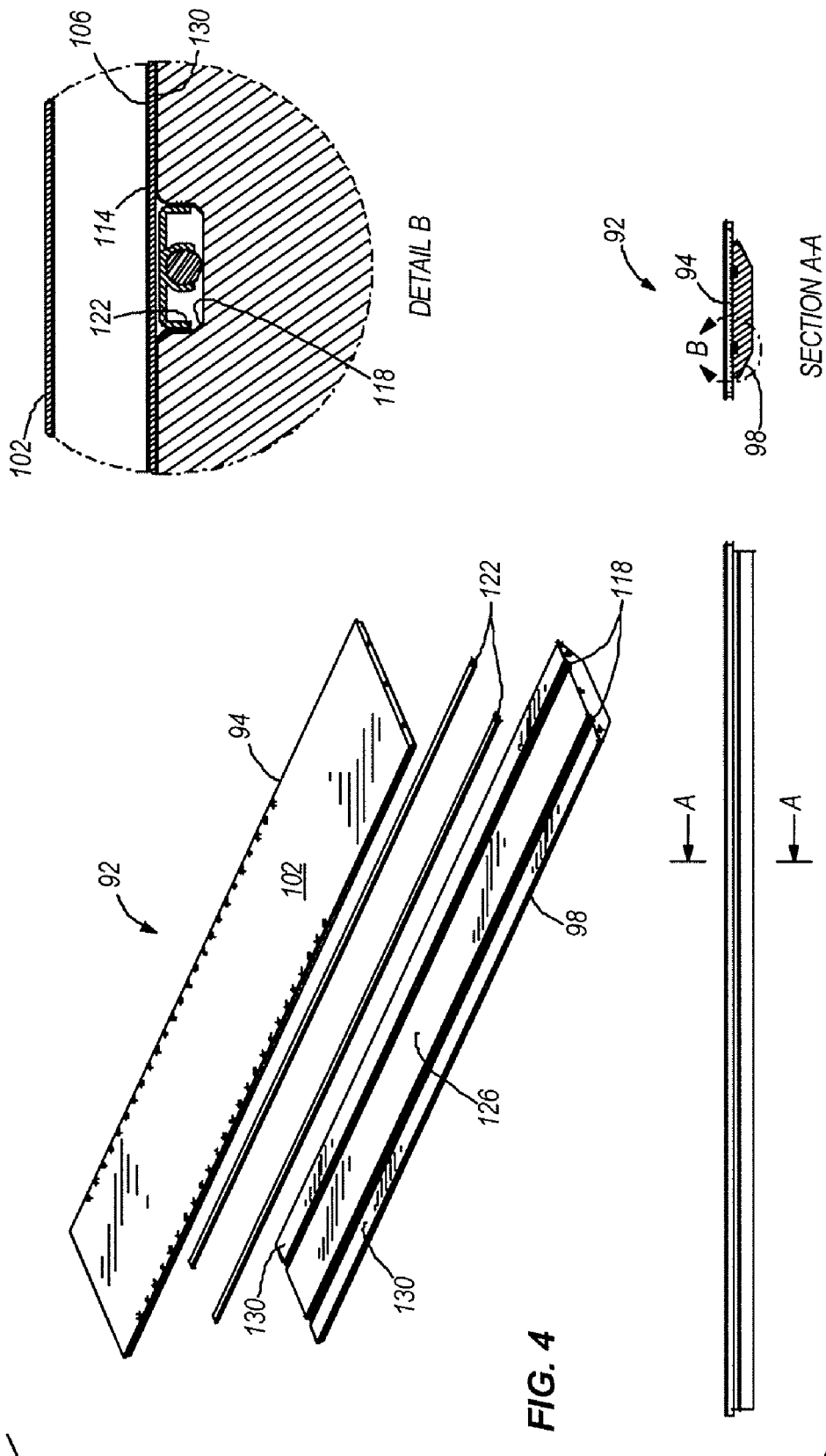
FIG. 4 is an exploded view of a table assembly of the patient support device of FIG. 3.
Figure 5:
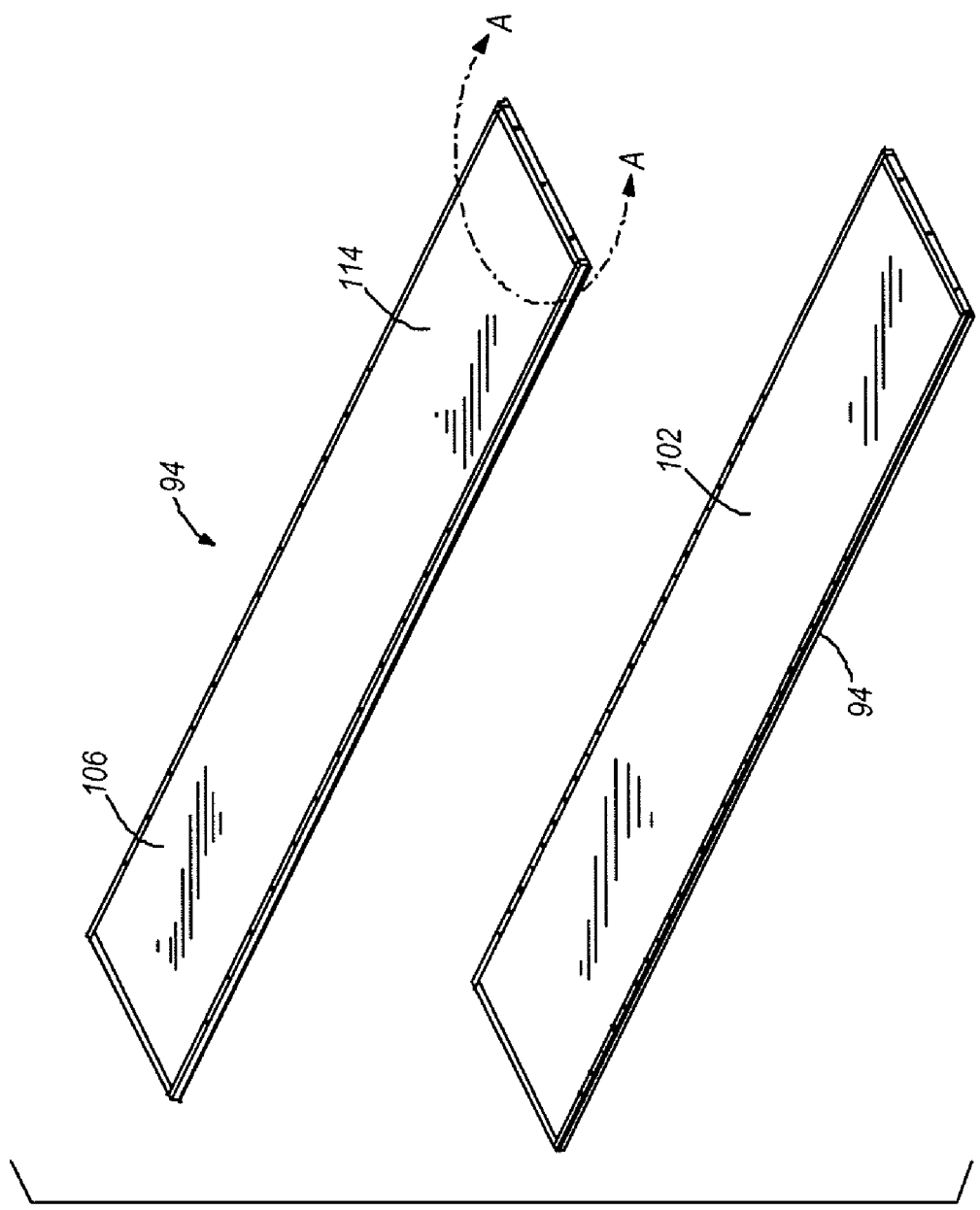
FIG. 5 is a perspective view of an upper support of the table assembly of FIG. 4.
Figure 6:
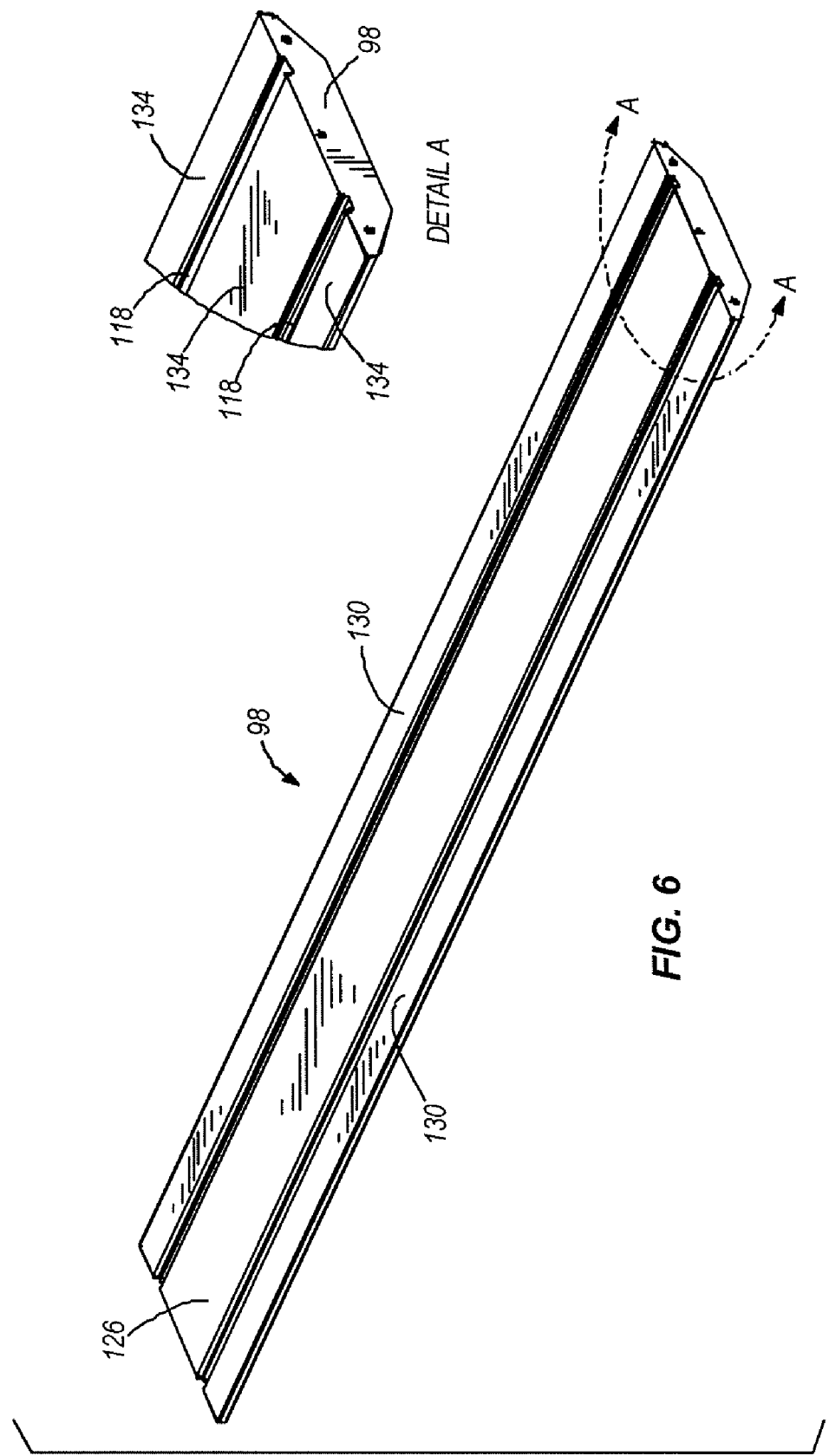
FIG. 6 is a perspective view of a lower support of the table assembly of FIG. 4.
Figure 7:
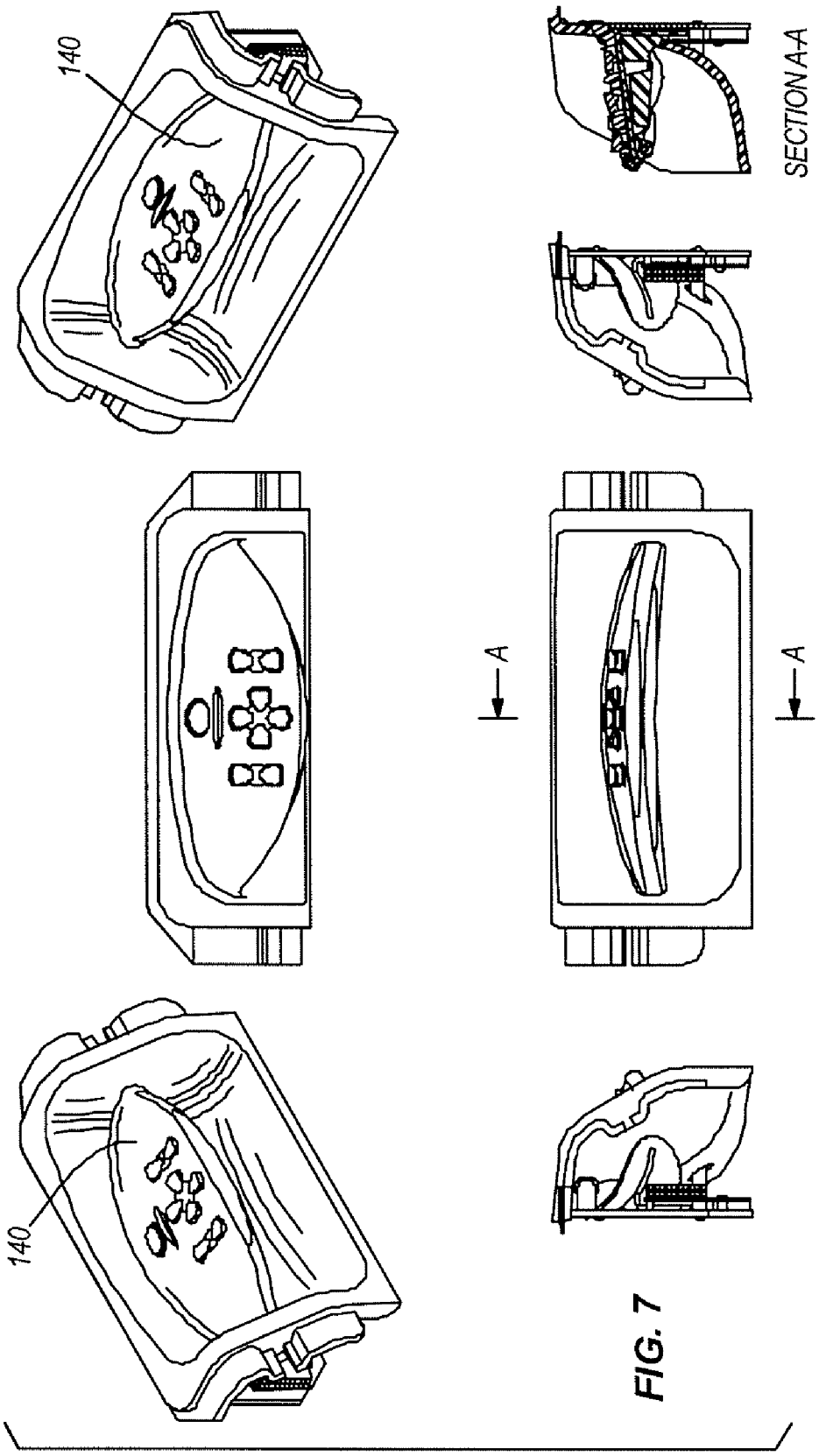
FIG. 7 is an assortment of views of a control keypad for use with the patient support device of FIG. 1.
Figure 8:
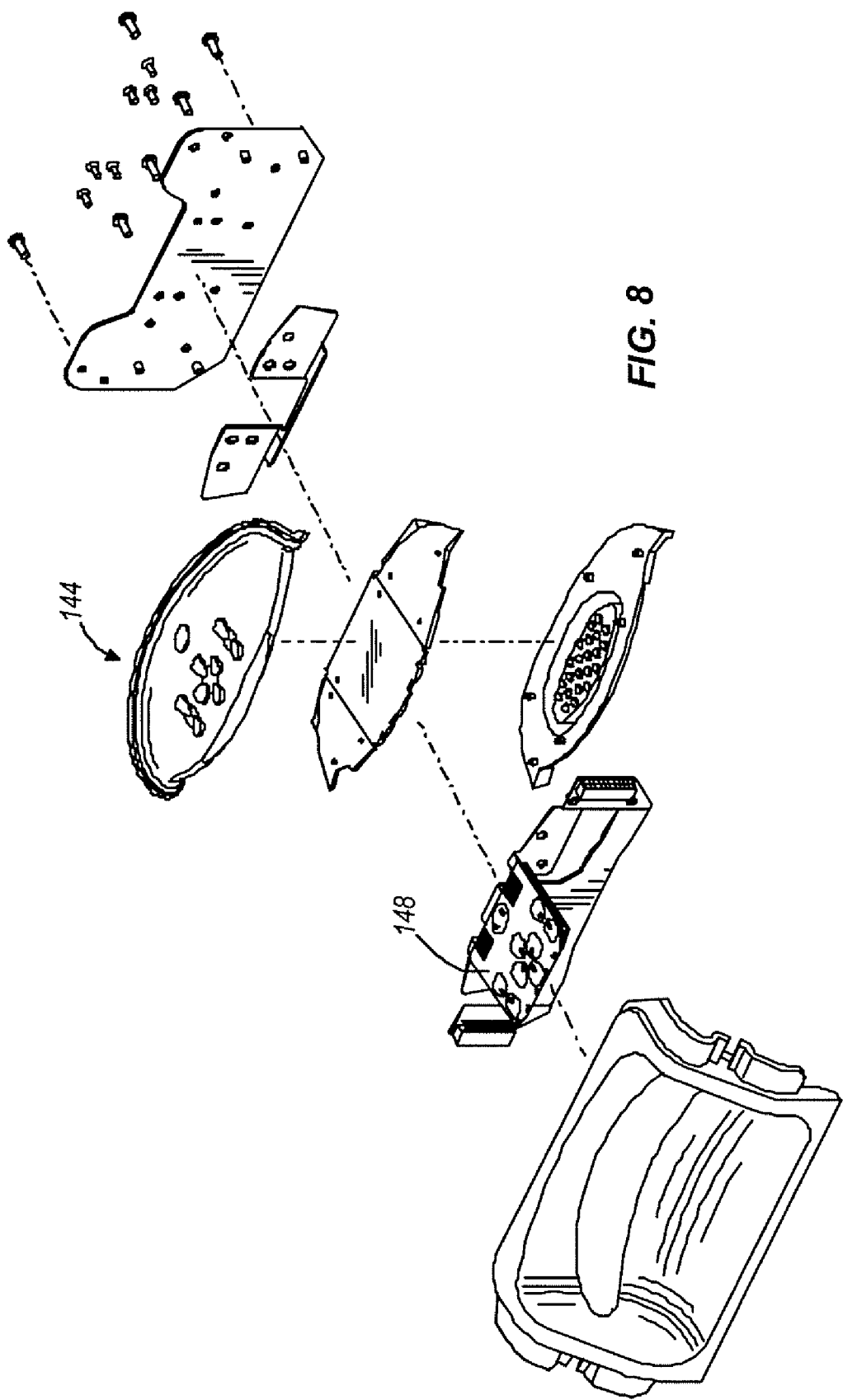
FIG. 8 is an exploded view of the keypad of FIG. 7.
Figure 9:
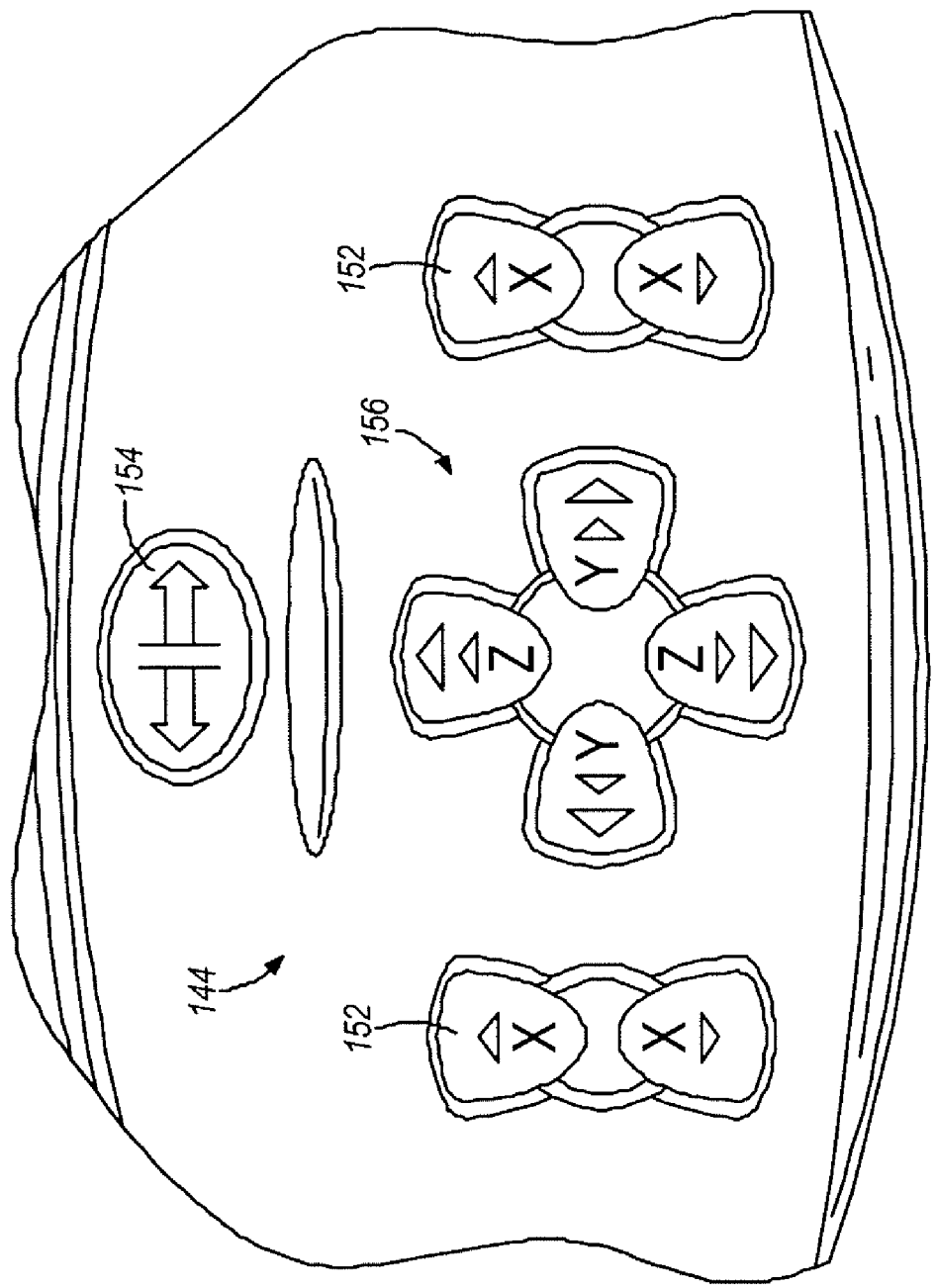
FIG. 9 is a front view of the keypad of FIG. 7, illustrating the control buttons in greater detail
Figure 10:
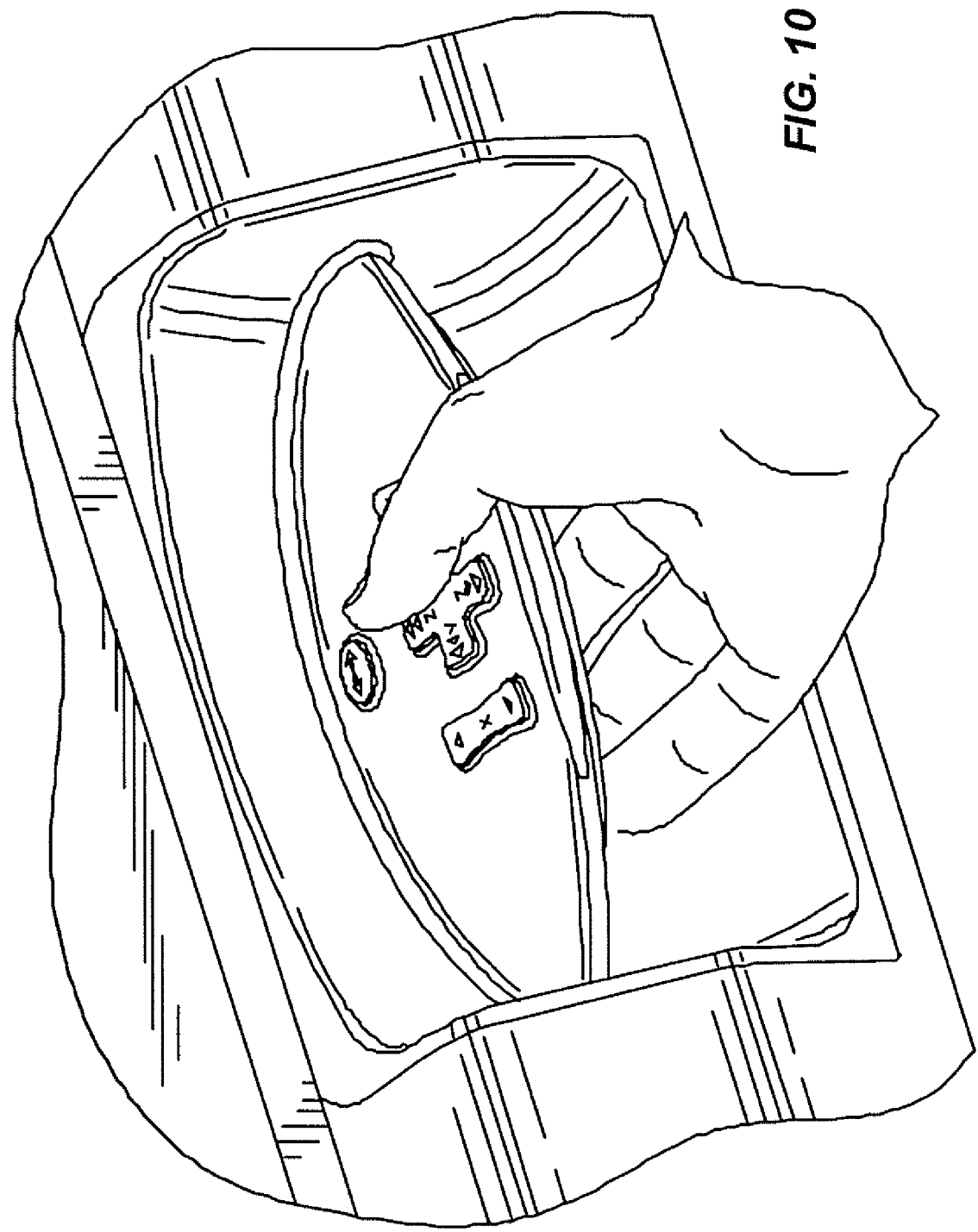
FIG. 10 is a perspective view of the keypad of FIG. 7, illustrating operation of the buttons by the operator of the patient support device
Figure 11:
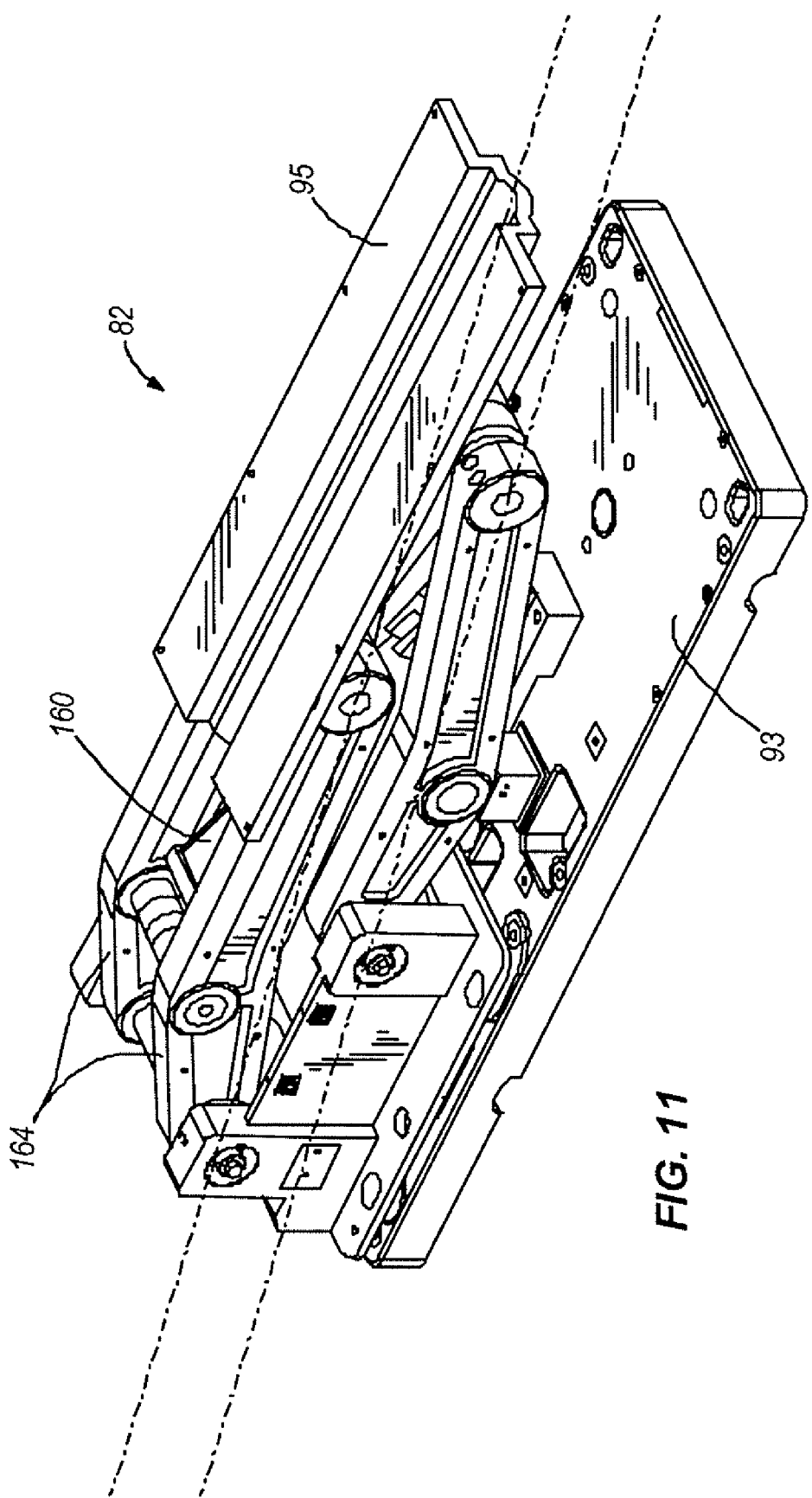
FIG. 11 is a perspective view of the patient support device of FIG. 3, shown in the lowered position.

With reference to FIGS. 3-6, the couch 82 includes a table assembly 92 coupled to a base 93 via a platform 95. The table assembly 92 includes an upper support 94 movably coupled to a lower support 98. With particular reference to FIG. 5, the upper support 94 is a substantially flat, rectangular support member on which the patient is supported during treatment. The upper support 94 is movable with respect to the lower support 98 to move the patient into and out of the radiation beam 30 during treatment. In the illustrated embodiment, the upper and lower supports 94, 98 are composed of a carbon fiber composite, though other compositions of the supports are possible.

The upper support 94 has an upper surface 102 and a lower surface 106 that contacts an upper surface 110 of the lower support 98. As shown in the illustrated embodiment, the lower surface 106 includes a bearing layer 114 that is intended to reduce friction between the lower surface 106 and the upper surface 110 of the lower support 98 when the upper support 94 is moved with respect to the lower support 98. In the illustrated embodiment, the bearing layer 114 is a polyimide laminate that is coupled to the lower surface 106 using a pressure sensitive adhesive. In the illustrated embodiment, the laminate is Kapton™, available from DuPont. When the upper support 94 moves with respect to the lower support 98, any friction that builds up between the supports can interrupt the operation of the electronics that control the operation of the couch 82 and thus minimizing the friction is one of the goals of the invention. Further, when the supports are composed of the carbon fiber composite, the friction can cause the creation and build-up of carbon dust, which can cause problems with couch operation. Additionally, if the surfaces of the upper and lower supports 94, 98 were to contact each other directly, the contact would result in additional wear and possible warping of the supports themselves, which may not only reduce the precision with which the couch can operate to position a patient, but can also cause couch failure.

With reference to FIG. 4, the lower support 98 includes two channels 118 that are designed to receive and house wiring necessary for the operation of the couch 82. In some embodiments, a retaining member 122 is placed over the wiring within the channels 118 to hold the wiring in place and force the wiring to lie straight within the channels 118 to reduce the possibility of the wiring being pinched between the upper support 94 and the lower support 98. Furthermore, it is desirable to hold the wires in a straight and constant position for image reproducibility. Both the retaining member 122 and the outer sheathing of the wiring itself are composed of radiation resistant material to provide for the protection and proper functioning of the wiring in the high radiation environment of the couch 82. The spacing and design of the channels 118 is selected to separate the power lines from the data lines to prevent interference problems that occur when the two lines are not sufficiently spaced.

The table assembly 92 is movable in the X, Y, and Z directions, as illustrated in FIG. 1. Positioning of the table assembly 92, and thus the position of the patient, with respect to the gantry 18 and the radiation beam 30 must be precise to ensure that the radiation is delivered to the proper areas of the patient. The movement of the table assembly 92 is controlled by the couch operator using a control keypad 140, illustrated in FIGS. 7-10. Once the user actuates the buttons 144 of the keypad 140, the table assembly 92 will move at the direction of the user.

Another feature of the couch 82 according to the present invention is that lateral motion (i.e., motion in the X direction) is automatically controlled, and the lateral motion of both ends of the table assembly 92 is synchronized. In conventional patient support tables, lateral motion adjustment is accomplished using a knob or screw that is manually turned to adjust position in the lateral direction. Not only is this adjustment manual, but also the adjustment of each end of the support table must be done separately and there is no mechanism that synchronizes the position of the table ends. This can cause patient positioning errors as one end may be moved to a more extreme lateral position than the other and obtaining a true, synchronized position of both ends in the lateral direction is very difficult.

In addition, synchronization of the ends is also useful in assuring reliable and reproducible imaging results. In a system such as the system of the present invention where a patient on the couch 82 is subject to radiation for the purposes of taking an image of that patient, anything in the path between the radiation source and the detector that feeds data to the system to produce the image can impact the quality of the images. The wiring that runs underneath the table assembly 92 as discussed above can interfere with the quality of the images taken, and may result in an artifact on the resulting images that a therapist or physician will want to take into consideration when reviewing the resulting images. The channels 118 in the lower support 98 discussed above function to keep the wiring separated and contained. By synchronizing the motion of the ends of the table assembly 92 in addition to knowing the position of the channels 118, the physician/therapist has predictable artifacts that can be effectively eliminated by the physician/therapist when viewing the images because those artifacts will be in predictable locations, will be correctable, and the images will be reproducible. Without the synchronization, the artifacts would be more of a distraction to the user.

Figure 13:
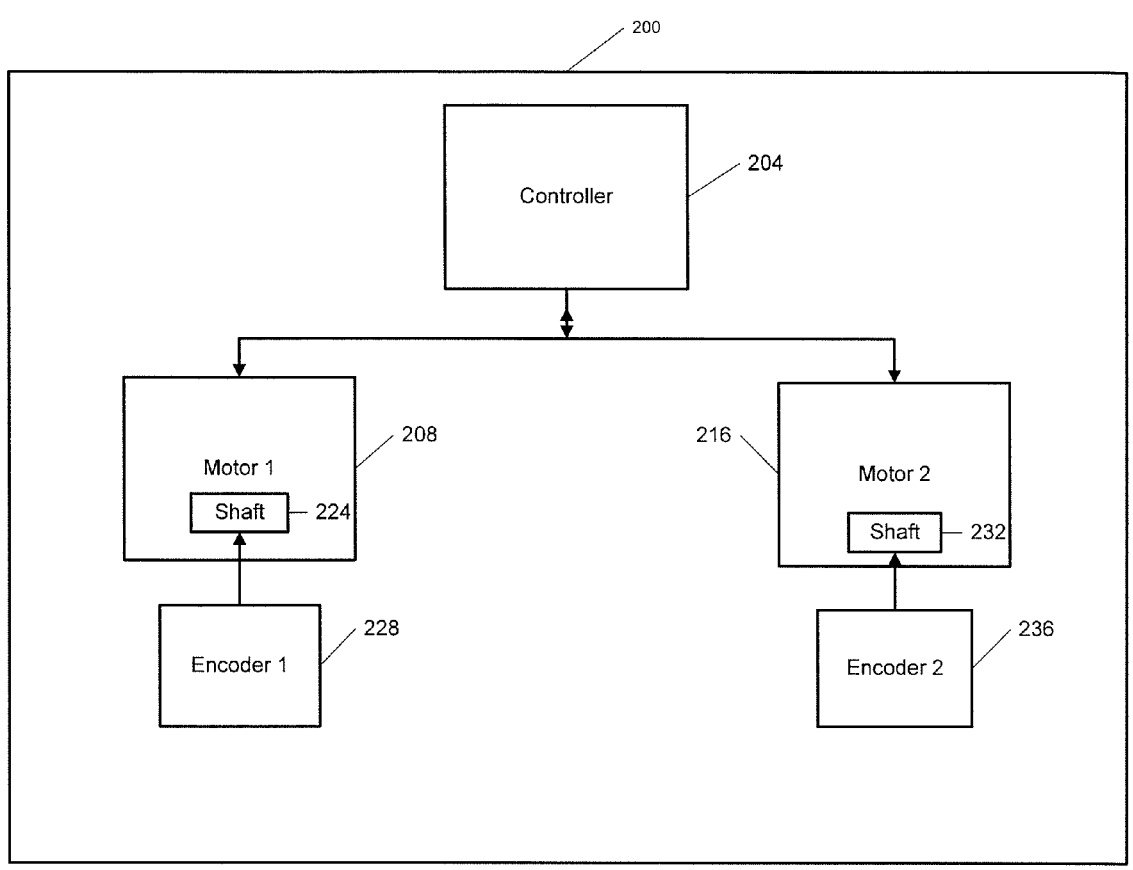
FIG. 13 is a diagram of a lateral motion control system according to one embodiment of the present invention.

The couch 82 includes a lateral motion control system 200 according to one embodiment of the present invention as illustrated in FIG. 13. The lateral motion control system 200 includes a controller 204 electrically coupled to a first motor 208 positioned near a first end 212 of the table assembly 92 and electrically coupled to a second motor 216 positioned near a second end 220 of the table assembly 92. The first motor 208 includes a shaft 224 and an encoder 228 coupled to the shaft 224. The second motor 216 includes a shaft 232 and an encoder 236 coupled to the shaft 232. The encoders 228, 236 communicate with the controller 204 to transmit position data of the respective motor shaft. The controller 204 receives motion instructions from the keypad 140. The controller 204 includes computer code that compares the position data from the encoders 228, 236 to ensure that the shafts 224, 232 of the respective motors 208, 216 at both ends of the table assembly 92 are synchronized. The controller 204 moves the table assembly 92 in both axes (X and Y) at the same time and looks for yaw at the same time as the motion. The encoders 228, 236 are absolute encoders that incorporate feedback, such as SSI or other appropriate types of feedback, to make the synchronicity possible.

The use of motors 208, 216 in conjunction with the linear absolute feedback of the encoders 228, 236 allow the system to be able to detect yawing and crab motion of the table assembly 92 and display that information for the operator. The fact that the feedback is linear allows the user to see what is happening on the load side as well. All of this feedback information is possible due to the separation of the feedback lines (data wires) from those supplying power in the channels 118 as described above.

Y axis motion is controlled using a stepper motor. While the table assembly 92 is moving, absolute linear feedback is used to servo the table assembly 92 to keep it within tolerance limits, thereby improving the accuracy with which couch motion can be controlled. Furthermore, the Y axis motion control has the benefit of being able to detect obstructions or impending couch collisions (such as with the gantry), causing the couch to stop prior to the collision. Collision detection occurs dynamically with continuous double-checking on couch position. Any error propagation is displayed to the end user on the PCP.

Additional features of the invention can be found in the following claims.

What is claimed is:

1. A patient support device comprising:
   a base;
   a table assembly configured to support a patient and having a longitudinal axis, the table assembly including
   a lower support, and
      an upper support movable with respect to the lower support, the upper support including a first end and a second end;
   a controller electrically coupled to the table assembly and configured to instruct the table assembly to move in a first direction along the axis, in a lateral direction with respect to the axis, and in a vertical direction with respect to the axis;
   a first motor coupled to the upper support;
   a first encoder in communication with the controller and configured to detect a first lateral position of the first end of the upper support;
   a second motor coupled to the upper support; and
   a second encoder in communication with the controller and configured to detect a second lateral position of the second end of the upper support, the controller configured to receive and compare the first lateral position and the second lateral position, the controller configured to communicate instructions to the first motor and the second motor to substantially synchronize the first lateral position and the second lateral position.

2. The patient support device of claim 1 further comprising a keypad coupled to the table assembly, and wherein the controller is further configured to receive instructions from a user via the keypad to substantially synchronize the first lateral position and the second lateral position.

3. The patient support device of claim 1 wherein one of the first encoder and the second encoder is further configured to detect yaw motion of the upper support while the upper support is moved in a lateral direction with respect to the axis.

4. The patient support device of claim 1 wherein one of first encoder and the second encoder is further configured to detect crab motion of the upper support while the upper support is moved in a lateral direction with respect to the axis.

5. The patient support device of claim 1 further comprising a stepper motor electrically coupled to the table assembly and configured to move the upper support a vertical direction with respect to the axis.

6. A radiation therapy treatment system comprising:
   a gantry;
   a table assembly configured to support a patient, the table assembly including
   a lower support, and
      an upper support movable with respect to the lower support, the upper support including a first end and a second end;
   a controller electrically coupled to the table assembly and configured to instruct the table assembly to move in a first direction into the gantry, in a lateral direction with respect to the first direction, and in a vertical direction with respect to the first direction; and
   a lateral motion control system in communication with the controller, the lateral motion control system configured to detect a lateral position of the first end of the upper support and a lateral position of the second end of the upper support and output the lateral positions of the first end and the second end, and
   wherein the lateral motion control system is further configured to compare the positions of the first end and the second end.

7. The radiation therapy treatment system of claim 6 wherein the lateral motion control system is further configured to communicate instructions to the controller to synchronize the positions of the first end and the second end.

8. The radiation therapy treatment system of claim 6 wherein the lateral motion control system is further configured to communicate instructions to the controller to synchronize the positions of the first end and the second end.

9. The radiation therapy treatment system of claim 6 wherein the controller is further configured to receive instructions from a user via a keypad to move the table assembly in one of the first direction, in a lateral direction with respect to the first direction, and in a vertical direction with respect to the first direction.

10. The radiation therapy treatment system of claim 9 wherein the controller is further configured to receive instructions from a user via a keypad to synchronize the position of the first end with the position of the second end.

11. The radiation therapy treatment system of claim 6 wherein the controller is further configured to receive instructions from a user via a keypad to synchronize the position of the first end with the position of the second end.

12. The radiation therapy treatment system of claim 6 wherein the lateral motion control system includes a first motor including a shaft coupled to the first end of the upper support, a first encoder coupled to the shaft and configured to detect a first position of the shaft of the first motor, a second motor including a shaft coupled to the second end of the upper support, and a second encoder coupled to the shaft and configured to detect a second position of the shaft of the second motor.

13. The radiation therapy treatment system of claim 12 wherein the controller is configured to receive and compare the first position and the second position, the controller further configured to communicate instructions to the first motor and the second motor to substantially synchronize the first position and the second position.

14. A method comprising:
   detecting a position of a first end of a table assembly for a radiation therapy treatment system;
   detecting a position of a second end of the table assembly;
   comparing the position of the first end with the position of the second end; and
   substantially synchronizing the position of the first end with the position of the second end.

15. The method of claim 14 wherein substantially synchronizing the position of the first end with the position of the second end occurs during movement of the table assembly.

16. The method of claim 15 wherein the movement of the table assembly is in a lateral direction with respect to a base that supports the table assembly.

17. A radiation therapy treatment system comprising:
   a gantry;
   a table assembly configured to support a patient, the table assembly including
   a lower support, and an upper support movable with respect to the lower support, the upper support including a first end and a second end;

a controller electrically coupled to the table assembly and configured to instruct the table assembly to move in a first direction into the gantry, in a lateral direction with respect to the first direction, and in a vertical direction with respect to the first direction; and a lateral motion control system in communication with the controller, the lateral motion control system configured to detect a lateral position of the first end of the upper support and a lateral position of the second end of the upper support and output the lateral positions of the first end and the second end, and wherein the lateral motion control system is further configured to communicate instructions to the controller to synchronize the positions of the first end and the second end.

18. The radiation therapy treatment system of claim 17 wherein the lateral motion control system includes a first motor including a shaft coupled to the first end of the upper support, a first encoder coupled to the shaft and configured to detect a first position of the shaft of the first motor, a second motor including a shaft coupled to the second end of the upper support, and a second encoder coupled to the shaft and configured to detect a second position of the shaft of the second motor.

19. The radiation therapy treatment system of claim 18 wherein the controller is configured to receive and compare the first position and the second position, the controller further configured to communicate instructions to the first motor and the second motor to substantially synchronize the first position and the second position.

20. The radiation therapy treatment system of claim 17 wherein the controller is further configured to receive instructions from a user via a keypad to move the table assembly in one of the first direction, in a lateral direction with respect to the first direction, and in a vertical direction with respect to the first direction.

* * * * *